United States Patent [19]

Kees, Jr.

[11] Patent Number: 4,777,950

[45] Date of Patent: * Oct. 18, 1988

[54] VASCULAR CLIP

[75] Inventor: George Kees, Jr., Alexandria, Ky.

[73] Assignee: Kees Surgical Specialty Co., Wilder, Ky.

[ * ] Notice: The portion of the term of this patent subsequent to Apr. 28, 2004 has been disclaimed.

[21] Appl. No.: 850,859

[22] Filed: Apr. 11, 1986

[51] Int. Cl.⁴ .............................................. A61B 17/12
[52] U.S. Cl. .................................. 128/325; 128/346; 24/546
[58] Field of Search ............... 128/346, 325, 326, 354; 24/67 R, 67.9, 489, 531, 546, 547, 551, 552, 566, 567

[56] References Cited

U.S. PATENT DOCUMENTS

| 26,975 | 4/1897 | Evans | 24/551 |
| 1,267,694 | 5/1918 | Ralston | 24/549 |
| 1,892,678 | 1/1933 | McIntyre et al. | 24/551 |
| 1,963,538 | 6/1934 | Wareing | 24/545 |
| 2,046,781 | 7/1936 | Head | 24/531 |
| 2,638,103 | 5/1953 | Fuscaldo | 24/557 |
| 3,166,819 | 1/1965 | Robbins | 128/346 |
| 3,827,438 | 8/1974 | Jees, Jr. | 128/346 |
| 4,024,868 | 5/1977 | Williams | 128/346 |
| 4,192,315 | 3/1980 | Hilzinger | 128/346 |
| 4,269,190 | 5/1981 | Behney | 128/346 |
| 4,360,023 | 11/1982 | Sugita et al. | 128/346 |
| 4,444,187 | 4/1984 | Perlin | 128/346 |
| 4,658,822 | 4/1987 | Kees, Jr. | 24/546 |
| 4,660,558 | 4/1987 | Kees, Jr. | 24/546 |

FOREIGN PATENT DOCUMENTS

| 0390558 | 2/1924 | Fed. Rep. of Germany | 24/557 |
| 9100 | 10/1894 | Switzerland | 24/531 |
| 1192794 | 11/1985 | U.S.S.R. | 128/346 |

Primary Examiner—Stephen C. Pellegrino
Assistant Examiner—Ralph Lewis
Attorney, Agent, or Firm—Paul A. Coletti

[57] ABSTRACT

A one-piece vascular clip which includes a central helical spring section, first connecting sections joined by the spring section, second connecting sections extending from the first connecting sections to cross. First jaw sections extend from the second connecting sections. A return bend jaw section extends from each of the first jaw sections parallel and adjacent to the associated first jaw section. A horn extends outwardly from each of the return bend jaw sections.

3 Claims, 1 Drawing Sheet

VASCULAR CLIP

BACKGROUND OF THE INVENTION

This invention relates to a vascular clip. More particularly, this invention relates to a clip which can be mounted on a blood vessel to close the vessel or a portion thereof.

An object of this invention is to provide a vascular clip of small size formed from a single length of spring wire provided with jaws formed to double width wire sections and provided with horns or projections which preclude the jaw contacting portions of the jaws from advancing beyond their contact plane when laterally misaligned into non-opposed relation and therefore maintain alignment between jaws even if jaws are mispositioned.

SUMMARY OF THE INVENTION

Briefly, this invention provides a vascular clip formed from a single length of spring wire. A central section of the length is formed to a single spring loop. First connecting sections extend outwardly from ends of the central section. Second connecting sections extend from outer ends of the first connecting sections and cross. First jaw sections extend from ends of the second connecting sections. Return bend jaw sections extend from ends of the first jaw sections parallel and adjacent to the first jaw sections and attached thereto, with each first jaw section being opposed to the return bend section connected to the other first jaw section. Horn sections extend from the return bend sections into position for preventing the first jaw sections passing each other.

The above and other objects and features of the invention will be apparent to those skilled in the art to which this invention pertains from the following detailed description and the drawings, in which:

DESCRIPTION OF PRESENTLY PREFERRED EMBODIMENT

Figure 1:
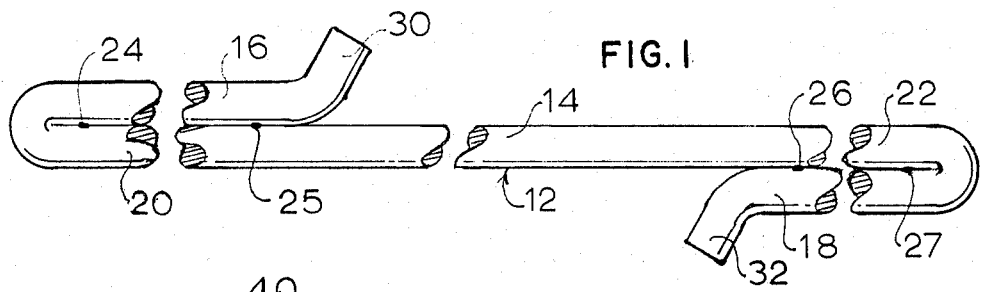
FIG. 1 is a fragmentary plan view of a blank from which a vascular clip constructed in accordance with an embodiment of this invention is constructed.

In the following detailed description and the drawing, like reference characters indicate like parts.

Figure 2:
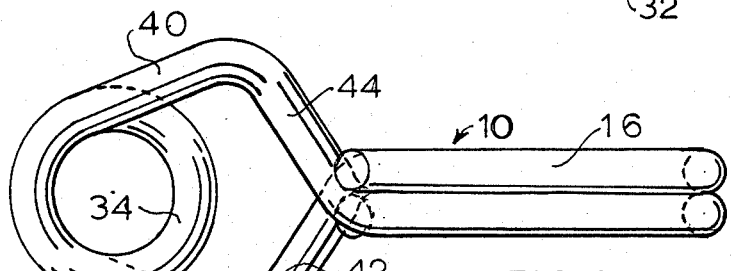
FIG. 2 is a view in side elevation of the clip.
Figure 3:
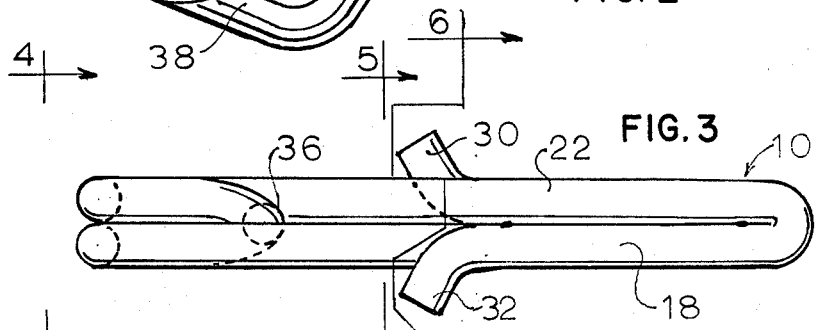
FIG. 3 is a bottom plan view of the clip.
Figures 4, 5, 6:
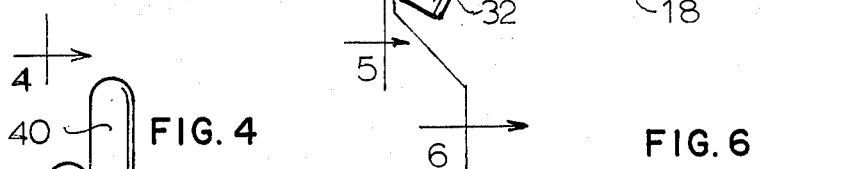
FIG. 4 is a view in end elevation looking in the direction of the arrows 4—4 in FIG. 3.
FIG. 5 is a view in section taken on the line 5—5 in FIG. 3.
FIG. 6 is a view in section taken generally on the line 6—6 in FIG. 3.

In FIGS. 2 and 3 is shown a vascular clip 10 constructed in accordance with an embodiment of this invention. The clip 10 is formed from a single length or blank 12 (FIG. 1) of spring wire. The blank 12 includes a central section 14. Return bend jaw sections 16 and 18 are bent to be parallel and adjacent to first jaw sections 20 and 22, respectively, of the length at opposite ends of the central section 14. The return bend jaw sections 16 and 18 are welded to the first jaw sections 20 and 22, respectively, as indicated by welds 24, 25, 26 and 27. End sections 30 and 32 of the length 12 outboard of the return bend jaw sections 16 and 18, respectively, are bent outwardly to form horn sections. As shown in FIG. 6, each of the return bend sections 16 and 18 is coplanar with the associated first jaw section and the associated horn section.

The central section 14 of the length 12 is formed to include a central spring section 34 consisting of a single loop or turn 36 with first connecting sections 38 and 40 extending outwardly of the loop 36 substantially tangentially thereof. Such connecting sections 42 and 44 extend from outer ends of the first connecting sections 38 and 40, respectively, and cross as shown in FIG. 2. The first jaw section 20 is integral with the second connecting section 42 and the first jaw section 22 is integral with the second connecting section 44.

Figure 7:
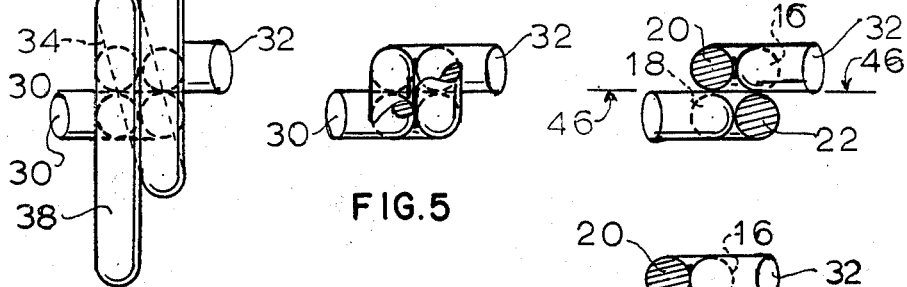
FIG. 7 is a view similar to FIG. 6, but in which the jaws are shown in laterally displaced relation.

As shown in FIG. 7, the jaws may be shifted laterally relative to each other, but cooperation of jaws with horns limit their contact surfaces to approach no further toward each other than the contact plane 46 and thus remain capable of moving toward or into alignment without mechanical interference of the jaws with one another.

The clip 10 can be manipulated and opened by means of an appropriate tool (not shown) such as one of the tools shown in my U.S. Pat. Nos. 2,876,778 and 3,827,438. The open clip can be positioned to close an aneurysm, blood vessel or the like (not shown) and can be released to seal off the aneurysm, blood vessel or the like.

The vascular clip illustrated in the drawing and described above is subject to structural modification without departing from the spirit and scope of the appended claims.

Having described my invention, what I claim as new and desire to secure by Letters Patent is:

1. A one-piece vascular clip formed from a length of spring wire which comprises a central helical spring section, first connecting sections joined by the spring section, second connecting sections extending from the first connecting sections and crossing, first jaw sections extending from the second connecting sections, a respective return bend jaw section extending from each of the first jaw sections parallel and adjacent to the associated first jaw section, and a horn extending outwardly from each of the return bend jaw sections, each of the return bend jaw sections being coplanar with the associated first return bend jaw section and the associated horn, the horns being engageable with the second connecting sections to preclude the jaw contacting portions of the jaws from advancing beyond their contact plane when laterally misaligned into non-opposed relation to maintain the jaw sections and the return bend jaw sections in alignment.

2. A vascular clip as in claim 1 in which each return bend jaw section is attached to the associated first jaw section by means spaced from the place where the return bend jaw section extends from the associated first jaw section.

3. A one-piece vascular clip as in claim 1 in which the central helical spring section includes a single convolution and that each return bend jaw section is opposite an opposed first jaw section.

* * * * *